(12) United States Patent
Anderson et al.

(10) Patent No.: US 9,514,959 B2
(45) Date of Patent: Dec. 6, 2016

(54) FLUOROCARBON MOLECULES FOR HIGH ASPECT RATIO OXIDE ETCH

(71) Applicants: L'AIR LIQUIDE, SOCIETE ANONYME POUR L'ETUDE ET L'EXPLOITATION DES PROCEDES GEORGES CLAUDE, Paris (FR); Curtis Anderson, Victori, MN (US); Rahul Gupta, Newark, DE (US); Vincent M. Omarjee, Menlo Park, CA (US); Nathan Stafford, Damascus, OR (US); Christian Dussarrat, Tokyo (JP)

(72) Inventors: Curtis Anderson, Victori, MN (US); Rahul Gupta, Newark, DE (US); Vincent M. Omarjee, Menlo Park, CA (US); Nathan Stafford, Damascus, OR (US); Christian Dussarrat, Tokyo (JP)

(73) Assignee: American Air Liquide, Inc., Fremont, CA (US)

( * ) Notice: Subject to any disclaimer, the term of this patent is extended or adjusted under 35 U.S.C. 154(b) by 0 days.

(21) Appl. No.: 14/439,831

(22) PCT Filed: Oct. 30, 2013

(86) PCT No.: PCT/US2013/067415
§ 371 (c)(1),
(2) Date: Apr. 30, 2015

(87) PCT Pub. No.: WO2014/070838
PCT Pub. Date: May 8, 2014

(65) Prior Publication Data
US 2015/0294880 A1 Oct. 15, 2015

Related U.S. Application Data

(60) Provisional application No. 61/720,139, filed on Oct. 30, 2012.

(51) Int. Cl.
*H01L 21/3065* (2006.01)
*H01L 21/3213* (2006.01)
(Continued)

(52) U.S. Cl.
CPC ......... *H01L 21/32137* (2013.01); *C07C 21/18* (2013.01); *C07C 23/06* (2013.01);
(Continued)

(58) Field of Classification Search
None
See application file for complete search history.

(56) References Cited

U.S. PATENT DOCUMENTS 4,711,698 A * 12/1987 Douglas ............ H01L 21/31116
204/192.32
6,051,504 A 4/2000 Armacost et al.
(Continued)

FOREIGN PATENT DOCUMENTS

DE 11 2008 003598 12/2010
EP 0 763 850 3/1997
(Continued)

OTHER PUBLICATIONS

Flamm, D.L. et al., "Plasma etching: an introduction—plasmas, materials interactions," Dennis M. Manos and Daniel L. Flamm, editors, Academic Press, Inc. 1989, 12-13.
(Continued)

*Primary Examiner* — Jiong-Ping Lu
(74) *Attorney, Agent, or Firm* — Patricia E. McQueeney

(57) ABSTRACT

Etching gases are disclosed for plasma etching channel holes, gate trenches, staircase contacts, capacitor holes, contact holes, etc., in Si-containing layers on a substrate and plasma etching methods of using the same. The etching gases are trans-1,1,1,4,4,4-hexafluoro-2-butene; cis-1,1,1,4,4,4-hexafluoro-2-butene; hexafluoroisobutene; hexafluorocyclobutane (trans-1,1,2,2,3,4); pentafluorocyclobutane (1,1,2,2,3-); tetrafluorocyclobutane (1,1,2,2-); or hexafluorocyclobutane (cis-1,1,2,2,3,4). The etching gases may provide improved selectivity between the Si-containing layers and mask material, less damage to channel region, a straight vertical profile, and reduced bowing in pattern high aspect ratio structures.

20 Claims, 8 Drawing Sheets

(51) Int. Cl.
*H01L 21/311* (2006.01)
*C07C 21/18* (2006.01)
*C07C 23/06* (2006.01)

(52) U.S. Cl.
CPC ..... *H01L21/3065* (2013.01); *H01L 21/31116* (2013.01); *H01L 21/32136* (2013.01); *C07C 2101/04* (2013.01)

(56) References Cited

U.S. PATENT DOCUMENTS

| | | | |
|---|---|---|---|
| 6,322,715 B1 * | 11/2001 | Sekiya | H01L 21/3065 216/67 |
| 6,387,287 B1 | 5/2002 | Hung et al. | |
| 6,569,774 B1 | 5/2003 | Trapp | |
| 6,613,689 B2 | 9/2003 | Liu et al. | |
| 6,897,532 B1 | 5/2005 | Schwarz et al. | |
| 6,972,258 B2 | 12/2005 | Chu et al. | |
| 6,972,265 B1 | 12/2005 | Schwarz | |
| 7,153,779 B2 | 12/2006 | Trapp | |
| 8,436,216 B2 | 5/2013 | Sun et al. | |
| 8,614,151 B2 | 12/2013 | Benson et al. | |
| 2006/0243944 A1 | 11/2006 | Minor et al. | |
| 2008/0157022 A1 | 7/2008 | Singh et al. | |
| 2009/0176375 A1 * | 7/2009 | Benson | H01L 21/31116 438/719 |
| 2010/0190343 A1 * | 7/2010 | Aggarwal | C30B 25/16 438/694 |
| 2010/0264116 A1 * | 10/2010 | Suzuki | H01L 21/31116 216/67 |
| 2011/0028769 A1 | 2/2011 | Sun et al. | |
| 2011/0144216 A1 | 6/2011 | Hulse et al. | |
| 2011/0180941 A1 | 7/2011 | Hwang et al. | |
| 2012/0085959 A1 * | 4/2012 | Uenveren | C08J 9/146 252/2 |
| 2012/0187330 A1 | 7/2012 | Singh et al. | |
| 2015/0097276 A1 | 4/2015 | Kim et al. | |

FOREIGN PATENT DOCUMENTS

| | | |
|---|---|---|
| EP | 2 258 789 | 12/2010 |
| EP | 2 287 271 | 2/2011 |
| JP | 3 253 215 B2 | 2/2002 |
| JP | 2012 188359 | 10/2012 |
| WO | WO 2008 154612 | 12/2008 |
| WO | WO 2009 019219 | 2/2009 |
| WO | WO 2009 117458 | 9/2009 |
| WO | WO 2010 100254 | 9/2010 |
| WO | WO 2012 010495 | 1/2012 |
| WO | WO 2012 067864 | 5/2012 |
| WO | WO 2013 059544 | 4/2013 |
| WO | WO 2013 123184 | 8/2013 |
| WO | WO 2014 160910 | 10/2014 |

OTHER PUBLICATIONS

Extreme Tech, "New manufacturing technology enables vertical 3D NAND transistors, higher capacity SSDs," http://www.extremetech.com/computing/131777-new-manufacturing-technology-enables-vertical-3d-transistors-higher-capacity-ssds, downloaded Jan. 27, 2015.
Nakamura, S. et al., "Comparative studies of perfluorocarbon alternative gas plasmas for contact hole etch," Japanese Journal of Applied Physics 42(1) No. 9A (2003) 5759-5764.
"Principles of Plasma Discharges and Materials Processing, $2^{nd}$ edition," M.A. Lieberman and A.J. Lichtenberg, editors, Wiley-Interscience, A. John Wiley & Sons Publication, 2005, 595-596.
International Search Report and Written Opinion for corresponding PCT/US2013/067415, Feb. 26, 2014.
Feirng, A.E. et al., New Amorphous Fluoropolymers of Tetrafluoroethylene with Fluorinated and Non-Fluorinated Tricyclononenes. Semiconductor Photoresists for Imaging at 157 and 193 nm; Macromolecules (2006), 39(9), 3252-3261.
Fields, R. et al., Carbene chemistry. Part I. Reactions of fluoroalkyldiazo compounds; Journal of the Chemical Society (Jun. 1964), 1881-9.
French, R.H. et al.; Novel hydrofluorocarbon polymers for use as pellicles in 157 nm semiconductor photolithography: fundamentals of transparency; Journal of Fluorine Chemistry (2003), 122(1), 63-80.
Henne, A.L. et al.; Perfluoro-2-butyne and its Hydrogenation Products; Journal of the American Chemical Society (1949), 71, 298-300.
Itakura, Y. et al.; Study of resist outgassing by F2 laser irradiation; Proceedings of SPIE—The International Society for Optical Engineering (2003), 5039 (Pt. 1, Advances in Resist Technology and Processing XX), 524-532.

* cited by examiner

FLUOROCARBON MOLECULES FOR HIGH ASPECT RATIO OXIDE ETCH

CROSS-REFERENCE TO RELATED APPLICATIONS

This application is a 371 of International PCT Application PCT/US2013/067415, filed Oct. 30, 2013, which claims priority to U.S. application No. 61/720,139, filed Oct. 30, 2012, the entire contents of each being incorporated herein by reference.

TECHNICAL FIELD

Etching gases are disclosed for plasma etching high aspect ratio channel holes, gate trenches, staircase contacts, capacitor holes, contact holes, etc., in Si-containing layers on a substrate. Plasma etching methods of using the same are also disclosed.

BACKGROUND

In memory applications in the semiconductor industries, such as DRAM and 2D NAND, plasma etching removes silicon-containing layers, such as SiO or SiN layers, from semiconductor substrates. For novel memory applications, such as 3D NAND (US 2011/0180941 to Hwang et al.), high aspect ratio etching of stacks of multiple SiO/SiN or SiO/poly-Si layers is critical. Preferably, the etchant has high selectivity between the mask and layers being etched. Furthermore, the etchant preferably etches the structure such that the vertical profile is straight with no bowing. The 3D NAND stack may include other silicon containing layers.

Traditionally, plasma etching is carried out using a plasma source which generates active species from a gas source (such as hydrogen-, oxygen-, or fluorine-containing gases). The active species then react with the Si-containing layers to form a fluorocarbon blocking overlayer and volatile species. The volatile species are removed by low pressure in the reactor, which is maintained by a vacuum pump. Preferably, the mask material is not etched by the active species. The mask material may comprise one of the following: photoresist, amorphous carbon, polysilicon, metals, or other hard masks that do not etch.

Traditional etch gases include $cC_4F_8$ (Octafluorocyclobutane), $C_4F_6$ (Hexafluoro-1,3-butadiene), $CF_4$, $CH_2F_2$, $CH_3F$, and/or $CHF_3$. These etch gases may also form polymers during etching. The polymer acts as protection layers on the sidewalls of the pattern etch structure. This polymer protection layer prevents the ions and radicals from etching the sidewalls which could cause non-vertical structures, bowing, and change of dimensions. A link between F:C ratio, SiO:SiN selectivity, and polymer deposition rate has been established (see, e.g., Lieberman and Lichtenberg, Principles of Plasma Discharges and Materials Processing, Second Edition, Wiley-Interscience, A John Wiley & Sons Publication, 2005, pp. 595-596; and FIG. 5 of U.S. Pat. No. 6,387,287 to Hung et al. showing an increased blanket selectivity to nitride for lower values of the F/C ratio).

Traditional dry etch methods, such as chemical etching, may not provide the necessary high aspect ratio (>20:1) because the high pressure conditions required during chemical etching may have detrimental effects on the aperture formed. Traditional chemistries, such as $C_4F_8$ and $C_4F_6$, may also be insufficient to provide the high aspect ratio required because the etch manufacturers are rapidly depleting the available parameters used to make the traditional chemistries work, such as RF power, RF frequency, pulsing schemes and tuning schemes. The traditional chemistries no longer provide sufficient polymer deposition on high aspect ratio side walls during the plasma etching process. Additionally, $C_xF_y$, wherein x and y each independently range from 1-4, polymers on sidewalls are susceptible to etching. As a result, the etched patterns may not be vertical and structures may show bowing, change in dimensions, and/or pattern collapse.

One key issue with etching of patterns is bowing. Bowing is often due to sidewall etching of the mask layer, which is often an amorphous carbon material. Amorphous carbon materials can be etch by oxygen radicals in the plasma which can cause increased opening of the mask and result in a bow-like etch structure.

U.S. Pat. No. 6,569,774 to Trapp discloses a plasma etch process for forming a high aspect ratio contact opening through a silicon oxide layer. Trapp discloses inclusion of nitrogen-comprising gases such as $NH_3$ to fluorocarbon ($C_xF_y$) and fluorohydrocarbon ($C_xF_yH_z$) etch chemistries to improve resist selectivity and reduce striations. A list of 35 fluorocarbon and fluorohydrocarbon chemistries are disclosed, but no structural formulae, CAS numbers, or isomer information are provided.

WO2010/100254 to Solvay Fluor GmbH discloses use of certain hydrofluoroalkenes for a variety of processes, including as an etching gas for semiconductor etching or chamber cleaning. The hydrofluoroalkenes may include a mixture of at least one compound selected from each of the following groups a) and b):
   a) (Z)-1,1,1,3-tetrafluorobut-2-ene, (E)-1,1,1,3-tetrafluorobut-2-ene, or 2,4,4,4-tetrafluorobut-1-ene, and
   b) 1,1,1,4,4,4-hexafluorobut-2-ene, 1,1,2,3,4,4-hexafluorobut-2-ene, 1,1,1,3,4,4-hexafluorobut-2-ene and 1,1,1,2,4,4-hexafluorobut-2-ene.

State of the art vertical 3D NAND structures require very high aspect ratios through alternating stacks of materials.

A need remains for new etch gas compositions for use in plasma applications to form high aspect ratio apertures.

NOTATION AND NOMENCLATURE

Certain abbreviations, symbols, and terms are used throughout the following description and claims, and include:

As used herein, the term "etch" or "etching" refers to a plasma etch process (i.e., a dry etch process) in which ion bombardment accelerates the chemical reaction in the vertical direction so that vertical sidewalls are formed along the edges of the masked features at right angles to the substrate (Manos and Flamm, Plasma Etching An Introduction, Academic Press, Inc. 1989 pp. 12-13). The etching process produces apertures, such as vias, trenches, channel holes, gate trenches, staircase contacts, capacitor holes, contact holes, etc., in the substrate.

The term "pattern etch" or "patterned etch" refers to etching a non-planar structure, such as a patterned mask layer on a stack of silicon-containing layers. The term "mask" refers to a layer that resists etching. The mask layer may be located above or below the layer to be etched.

The term "selectivity" means the ratio of the etch rate of one material to the etch rate of another material. The term "selective etch" or "selectively etch" means to etch one material more than another material, or in other words to have a greater or less than 1:1 etch selectivity between two materials.

As used herein, the indefinite article "a" or "an" means one or more.

The standard abbreviations of the elements from the periodic table of elements are used herein. It should be understood that elements may be referred to by these abbreviations (e.g., S refers to sulfur, Si refers to silicon, H refers to hydrogen, etc.).

As used herein, the abbreviation "NAND" refers to a "Negated AND" or Not AND" gate; the abbreviation "2D" refers to 2 dimensional gate structures on a planar substrate; the abbreviation "3D" refers to 3 dimensional or vertical gate structures, wherein the gate structures are stacked in the vertical direction; and the abbreviation "DRAM" refers to Dynamic Random-Access Memory.

Please note that the Si-containing films, such as SiN and SiO, are listed throughout the specification and claims without reference to their proper stoichiometry. The silicon-containing layers may include pure silicon (Si) layers, such as crystalline Si, polysilicon (polySi or polycrystalline Si), or amorphous silicon; silicon nitride ($Si_kN_l$) layers; or silicon oxide ($Si_nO_m$) layers; or mixtures thereof, wherein k, l, m, and n, inclusively range from 1 to 6. Preferably, silicon nitride is $Si_kN_l$, where k and l each range from 0.5 to 1.5. More preferably silicon nitride is $Si_1N_1$. Preferably silicon oxide is $Si_nO_m$, where n ranges from 0.5 to 1.5 and m ranges from 1.5 to 3.5. More preferably, silicon oxide is $SiO_2$ or $SiO_3$. The silicon-containing layer could also be a silicon oxide based dielectric material such as organic based or silicon oxide based low-k dielectric materials such as the Black Diamond II or III material by Applied Materials, Inc. The silicon-containing layers may also include dopants, such as B, C, P, As and/or Ge.

SUMMARY

Disclosed are methods for etching silicon-containing films. An etching gas is introduced into a plasma reaction chamber containing a silicon-containing film on a substrate. The etching gas is trans-1,1,1,4,4,4-hexafluoro-2-butene; cis-1,1,1,4,4,4-hexafluoro-2-butene; hexafluoroisobutene; hexafluorocyclobutane (trans-1,1,2,2,3,4); pentafluorocyclobutane (1,1,2,2,3-); tetrafluorocyclobutane (1,1,2,2-); or hexafluorocyclobutane (cis-1,1,2,2,3,4). An inert gas is introduced into the plasma reaction chamber. Plasma is activated to produce an activated etching gas capable of selectively etching the silicon-containing film from the substrate. The disclosed methods may include one or more of the following aspects:

- the etching gas being trans-1,1,1,4,4,4-hexafluoro-2-butene;
- the etching gas being cis-1,1,1,4,4,4-hexafluoro-2-butene;
- the etching gas being hexafluoroisobutene;
- the etching gas being hexafluorocyclobutane (trans-1,1,2,2,3,4);
- the etching gas being pentafluorocyclobutane (1,1,2,2,3-);
- the etching gas being tetrafluorocyclobutane (1,1,2,2-);
- the etching gas being hexafluorocyclobutane (cis-1,1,2,2,3,4);
- the activated etching gas selectively reacting with the silicon-containing film to form volatile by-products;
- removing volatile by-products from the plasma reaction chamber;
- the inert gas being selected from the group consisting of He, Ar, Xe, Kr, and Ne;
- the inert gas being Ar;
- mixing the etching gas and the inert gas prior to introduction to the plasma reaction chamber to produce a mixture;
- introducing the etching gas into the plasma reaction chamber separately from the inert gas;
- introducing the inert gas continuously into the plasma reaction chamber and introducing the etching gas into the plasma reaction chamber in pulses;
- the inert gas comprising approximately 50% v/v to approximately 95% v/v of a total volume of etching gas and inert gas introduced into the plasma reaction chamber;
- introducing an oxidizer into the plasma reaction chamber;
- not introducing an oxidizer into the plasma reaction chamber;
- the oxidizer being selected from the group consisting of $O_2$, CO, $CO_2$, NO, $N_2O$, and $NO_2$;
- the oxidizer being $O_2$;
- mixing the etching gas and the oxidizer prior to introduction into the plasma reaction chamber;
- introducing the etching gas into the plasma reaction chamber separately from the oxidizer;
- introducing the oxidizer continuously into the plasma reaction chamber and introducing the etching gas into the plasma reaction chamber in pulses;
- the oxidizer comprising approximately 5% v/v to approximately 100% v/v of a total volume of etching gas and oxidizer introduced into the plasma reaction chamber;
- the silicon-containing film comprising a layer of silicon oxide, silicon nitride, polysilicon, or combinations thereof;
- the silicon-containing film comprising oxygen atoms, nitrogen atoms, carbon atoms, or combinations thereof;
- the silicon-containing film not comprising silicon carbide;
- the silicon-containing film being selectively etched from an amorphous carbon layer;
- the silicon-containing film being selectively etched from a photoresist layer;
- the silicon-containing film being selectively etched from a polysilicon layer;
- the silicon-containing film being selectively etched from a metal contact layer;
- the silicon-containing film being a silicon oxide layer;
- the silicon oxide layer being a porous SiCOH film;
- selectively etching the silicon oxide layer from an amorphous carbon layer;
- selectively etching the silicon oxide layer from a photoresist layer;
- selectively etching the silicon oxide layer from a polysilicon layer;
- selectively etching the silicon oxide layer from a metal contact layer;
- selectively etching the silicon oxide layer from a SiN layer;
- the silicon-containing film being a silicon nitride layer;
- selectively etching the silicon nitride layer from an amorphous carbon layer;
- selectively etching the silicon nitride layer from a patterned photoresist layer;
- selectively etching the silicon nitride layer from a polysilicon layer;
- selectively etching the silicon nitride layer from a metal contact layer;
- selectively etching the silicon nitride layer from a SiO layer;
- selectively etching both silicon oxide and silicon nitride from a silicon layer;

producing an aperture in the silicon-containing film having an aspect ratio between approximately 10:1 and approximately 100:1;
producing a gate trench;
producing a staircase contact;
producing a channel hole;
producing a channel hole having an aspect ratio between approximately 60:1 and approximately 100:1;
producing a channel hole having a diameter ranging from approximately 40 nm to approximately 50 nm;
improving selectivity by introducing a second gas into the plasma reaction chamber;
the second gas being selected from the group consisting of $cC_4F_8$, $C_4F_6$, $CF_4$, $CHF_3$, $CFH_3$, $CH_2F_2$, COS, $CS_2$, $CF_3I$, $C_2F_3I$, $C_2F_5I$, and $SO_2$.
the second gas being $cC_5F_8$;
the second gas being $cC_4F_8$;
the second gas being $C_4F_6$;
mixing the etching gas and the second gas prior to introduction to the plasma reaction chamber;
introducing the etching gas into the plasma reaction chamber separately from the second gas;
introducing approximately 1% v/v to approximately 99.9% v/v of the second gas into the chamber;
activating the plasma by a RF power ranging from approximately 25 W to approximately 10,000 W;
the plasma reaction chamber having a pressure ranging from approximately 1 mTorr to approximately 10 Torr;
introducing the etching gas to the plasma reaction chamber at a flow rate ranging from approximately 5 sccm to approximately 1 slm;
maintaining the substrate at a temperature ranging from approximately −196° C. to approximately 500° C.;
maintaining the substrate at a temperature ranging from approximately −120° C. to approximately 300° C.;
maintaining the substrate at a temperature ranging from approximately −10° C. to approximately 40° C.;
measuring the activated etching gas by Quadropole mass spectrometer, optical emission spectrometer, FTIR, or other radical/ion measurement tool;
generating the plasma by applying RF power.

Also disclosed are plasma etching compounds selected from trans-1,1,1,4,4,4-hexafluoro-2-butene; cis-1,1,1,4,4,4-hexafluoro-2-butene; hexafluoroisobutene; hexafluorocyclobutane (trans-1,1,2,2,3,4); pentafluorocyclobutane (1,1,2,2,3-); tetrafluorocyclobutane (1,1,2,2-); or hexafluorocyclobutane (cis-1,1,2,2,3,4). The plasma etching compound has a purity of at least 99.9% by volume and less than 0.1% by volume trace gas impurities. A total content of nitrogen-containing and oxygen-containing gas contained in said trace gaseous impurities is less than 150 ppm by volume. The disclosed plasma etching compounds may include one or more of the following aspects:
the etching compound being trans-1,1,1,4,4,4-hexafluoro-2-butene;
the etching compound being cis-1,1,1,4,4,4-hexafluoro-2-butene;
the etching compound being hexafluoroisobutene;
the etching compound being hexafluorocyclobutane (trans-1,1,2,2,3,4);
the etching compound being pentafluorocyclobutane (1,1,2,2,3-);
the etching compound being tetrafluorocyclobutane (1,1,2,2-);
the etching compound being hexafluorocyclobutane (cis-1,1,2,2,3,4);
the oxygen-containing gas being water;
the oxygen-containing gas being $CO_2$;
the nitrogen-containing gas being $N_2$; and
the plasma etching compound having a water content of less than 20 ppm by weight.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
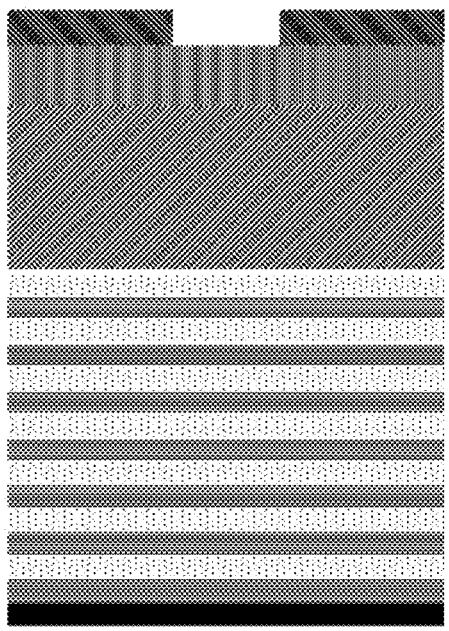
FIG. 1 is a diagram showing exemplary layers in a 3D NAND stack.
Figure 1:
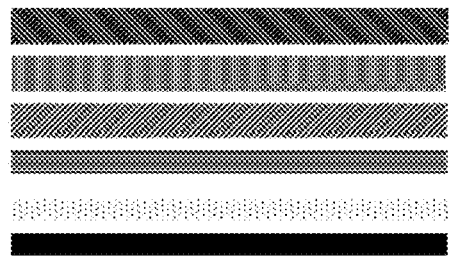

Etching gases are disclosed for plasma etching channel holes, gate trenches, staircase contacts, capacitor holes, contact holes, etc., in silicon-containing layers. The disclosed etching gases may provide higher selectivity to mask layers and no profile distortion in high aspect ratio structures.

The plasma etching gases may provide improved selectivity between the Si-containing layers and mask materials, less damage to channel region, and reduced bowing in pattern high aspect ratio structures. The plasma etching gases may also etch through alternating layers of polySi, SiO, and/or SiN, resulting in a vertical etch profile.

The following compounds form the disclosed plasma etching gases: trans-1,1,1,4,4,4-hexafluoro-2-butene; cis-1,1,1,4,4,4-hexafluoro-2-butene; hexafluoroisobutene; hexafluorocyclobutane (trans-1,1,2,2,3,4); pentafluorocyclobutane (1,1,2,2,3-); tetrafluorocyclobutane (1,1,2,2-); or hexafluorocyclobutane (cis-1,1,2,2,3,4). These compounds are commercially available.

The disclosed plasma etching gases are provided at greater than 99.9% v/v purity, preferably at greater than 99.99% v/v purity, and more preferably at greater than 99.999% v/v purity. The disclosed etching gases contain less than 0.1% by volume trace gas impurities with less than 150 ppm by volume of nitrogen-containing and oxygen-containing gases, such as $N_2$ and/or $H_2O$ and/or $CO_2$, contained in said trace gaseous impurities. Preferably, the water content in the plasma etching gas is less than 20 ppm by weight. The purified product may be produced by distillation and/or passing the gas or liquid through a suitable adsorbent, such as a 4A molecular sieve.

In one embodiment the disclosed plasma etching gas contains less than 5% v/v, preferably less than 1% v/v, more preferably less than 0.1% v/v, and even more preferably less than 0.01% v/v of any of its isomers. This embodiment may provide better process repeatability. This embodiment may be produced by distillation of the gas or liquid. In an alternate embodiment, the disclosed plasma etching gas may contain between 5% v/v and 50% v/v of one or more of its isomers, particularly when the isomer mixture provides improved process parameters or isolation of the target isomer is too difficult or expensive. For example, a mixture of isomers may reduce the need for two or more gas lines to the plasma reactor.

The CAS number for trans-1,1,1,4,4,4-hexafluoro-2-butene is 66711-86-2. Trans-1,1,1,4,4,4-hexafluoro-2-butene has a boiling point of 8.5° C.

The CAS number for cis-1,1,1,4,4,4-hexafluoro-2-butene is 692-49-9. Cis-1,1,1,4,4,4-hexafluoro-2-butene has a boiling point of 33° C.

The CAS number for trans-1,1,2,2,3,4-hexafluorocyclobutane is 23012-94-4. Trans-1,1,2,2,3,4-hexafluorocyclobutane has a boiling point of 27° C.

The CAS number for cis-1,1,2,2,3,4-hexafluorocyclobutane is 22819-47-2. Cis-1,1,2,2,3,4-hexafluorocyclobutane has a boiling point of 63° C.

The CAS number for hexafluoroisobutene is 382-10-5. Hexafluoroisobutene has a boiling point of 14.5° C.

The CAS number for 1,1,1,2,4,4,4-heptafluoro-2-butene is 760-42-9. 1,1,1,2,4,4,4-heptafluoro-2-butene has a boiling point of 8° C.

The CAS number for 1,1,2,2,3-pentafluorocyclobutane is 2253-02-3. 1,1,2,2,3-pentafluorocyclobutane has a boiling point of 53° C.

The CAS number for 1,1,2,2-tetrafluorocyclobutane is 374-12-9. 1,1,2,2-tetrafluorocyclobutane has a boiling point of 50° C.

Some of these compounds are gaseous at room temperature and atmospheric pressure. For the non-gaseous (i.e., liquid) compounds, the gas form may be produced by vaporizing the compounds through a conventional vaporization step, such as direct vaporization or by bubbling. The compound may be fed in liquid state to a vaporizer where it is vaporized before it is introduced into the reactor. Alternatively, the compound may be vaporized by passing a carrier gas into a container containing the compound or by bubbling the carrier gas into the compound. The carrier gas may include, but is not limited to, Ar, He, $N_2$, and mixtures thereof. Bubbling with a carrier gas may also remove any dissolved oxygen present in the etching gases. The carrier gas and compound are then introduced into the reactor as a vapor.

If necessary, the container containing the compound may be heated to a temperature that permits the compound to have a sufficient vapor pressure for delivery into the etching tool. The container may be maintained at temperatures in the range of, for example, approximately 25° C. to approximately 100° C., preferably from approximately 25° C. to approximately 50° C. More preferably, the container is maintained at room temperature (–25° C.) in order to avoid heating the lines to the etch tool. Those skilled in the art recognize that the temperature of the container may be adjusted in a known manner to control the amount of compound vaporized.

The disclosed etching gases are suitable for plasma etching channel holes, gate trenches, staircase contacts, capacitor holes, contact holes, etc., in one or more Si-containing layers and compatible with the current and future generation of mask materials because they induce little to no damage on the mask along with good profile of high aspect ratio structures. In order to achieve those properties, the disclosed etch gases may deposit an etch-resistant polymer layer during etching to help reduce the direct impact of the oxygen and fluorine radicals during the etching process. The disclosed compounds may also reduce damage to poly-Si channel structure during etching (see US 2011/0180941 to Hwang et al.). Preferably, the etching gas is both suitably volatile and stable during the etching process for delivery into the reactor/chamber.

The disclosed etching gases may be used to plasma etch silicon-containing layers on a substrate. The disclosed plasma etching method may be useful in the manufacture of semiconductor devices such as NAND or 3D NAND gates or Flash or DRAM memory. The disclosed etching gases may be used in other areas of applications, such as different front end of the line (FEOL) and back end of the line (BEOL) etch applications. Additionally, the disclosed etching gases may also be used for etching Si in 3D TSV (Through Silicon Via) etch applications for interconnecting memory substrates on logic substrates.

The plasma etching method includes providing a plasma reaction chamber having a substrate disposed therein. The plasma reaction chamber may be any enclosure or chamber within a device in which etching methods take place such as, and without limitation, Reactive Ion Etching (RIE), Dual Capacitively Coupled Plasma (CCP) with single or multiple frequency RF sources, Inductively Coupled Plasma (ICP), or Microwave Plasma reactors, or other types of etching systems capable of selectively removing a portion of the Si containing layer or generating active species. One of ordinary skill in the art will recognize that the different plasma reaction chamber designs provide different electron temperature control. Suitable commercially available plasma reaction chambers include but are not limited to the Applied Materials magnetically enhanced reactive ion etcher sold under the trademark eMAX™ or the Lam Research Dual CCP reactive ion etcher Dielectric etch product family sold under the trademark 2300® Flex™.

The plasma reaction chamber may contain one or more than one substrate. For example, the plasma reaction chamber may contain from 1 to 200 silicon wafers having from 25.4 mm to 450 mm diameters. The one or more substrates may be any suitable substrate used in semiconductor, photovoltaic, flat panel or LCD-TFT device manufacturing. The substrate will have multiple films or layers thereon, including one or more silicon-containing films or layers. The substrate may or may not be patterned. Examples of suitable layers include without limitation silicon (such as amorphous silicon, polysilicon, crystalline silicon, any of which may further be p-doped or n-doped with B, C, P, As, and/or Ge), silica, silicon nitride, silicon oxide, silicon oxynitride, tungsten, titanium nitride, tantalum nitride, mask materials such as amorphous carbon, antireflective coatings, photoresist materials, or combinations thereof. The silicon oxide layer may form a dielectric material, such as an organic based or silicon oxide based low-k dielectric material (e.g., a porous SiCOH film). An exemplary low-k dielectric material is sold by Applied Materials under the trade name Black Diamond II or III. Additionally, layers comprising tungsten or noble metals (e.g. platinum, palladium, rhodium or gold) may be used.

Figure 2:
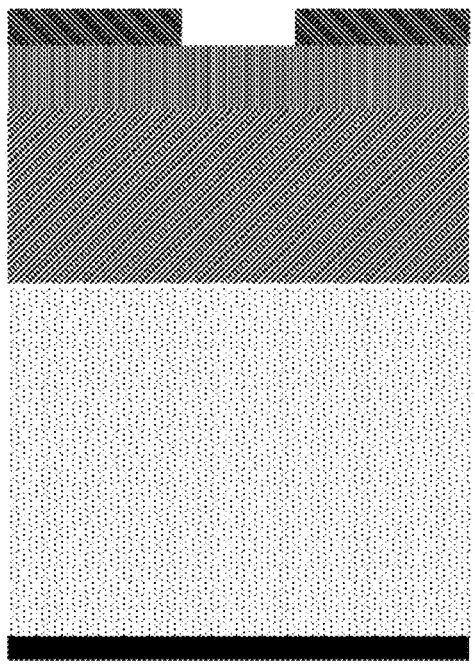
FIG. 2 is a diagram showing exemplary layers in a DRAM stack.
Figure 2:
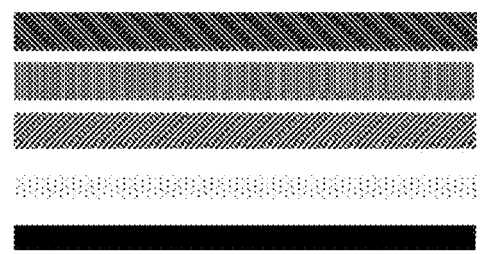

The substrate may include a stack of multiple silicon-containing layers thereon similar to those shown in FIGS. 1 and 2. In FIG. 1, a stack of seven SiO/SiN layers are located on top of a silicon wafer substrate (i.e., ONON or TCAT technology). One of ordinary skill in the art will recognize that some technologies replace the SiN layers with polySi layers (i.e., SiO/polySi layers in P-BICS technology). One of ordinary skill in the art will further recognize that the number SiO/SiN or SiO/poly-Si layers in the 3D NAND stack may vary (i.e., may include more or less than the seven SiO/SiN layers depicted). An amorphous carbon mask layer is located on top of the seven SiO/SiN layers. An antireflective coating layer is located on top of the amorphous carbon mask. A pattern photoresist layer is located on top of the antireflective coating. The stack of layers in FIG. 1 reflects layers similar to those used in a 3D NAND gate. In FIG. 2, a thick SiO layer is located on top of a silicon wafer substrate. An amorphous carbon mask layer is located on top of the thick SiO layer. An antireflective coating layer is located on top of the amorphous carbon mask. A pattern photoresist layer is located on top of the antireflective coating. The stack of layers in FIG. 2 reflects layers similar to those used in a DRAM gate. The disclosed etching gases selectively etch the silicon-containing layers (i.e., SiO, SiN, polySi) more than the amorphous carbon mask, antireflective coating, or photoresist layers. Those layers may be removed by other etching gases in the same or a different reaction chamber. One of ordinary skill in the art will recognize that the stack of layers in FIGS. 1 and 2 are provided for exemplary purposes only.

The disclosed etching gases are introduced into the plasma reaction chamber containing the substrate and silicon-containing layers. The gas may be introduced to the chamber at a flow rate ranging from approximately 0.1 sccm to approximately 1 slm. For example, for a 200 mm wafer size, the gas may be introduced to the chamber at a flow rate ranging from approximately 5 sccm to approximately 50 sccm. Alternatively, for a 450 mm wafer size, the gas may be introduced to the chamber at a flow rate ranging from approximately 25 sccm to approximately 250 sccm. One of ordinary skill in the art will recognize that the flow rate will vary from tool to tool.

An inert gas is also introduced into the plasma reaction chamber in order to sustain the plasma. The inert gas may be He, Ar, Xe, Kr, Ne, or combinations thereof. The etching gas and the inert gas may be mixed prior to introduction to the chamber, with the inert gas comprising between approximately 50% v/v and approximately 95% v/v of the resulting mixture. Alternatively, the inert gas may be introduced to the chamber continuously while the etching gas is introduced to the chamber in pulses.

The disclosed etching gas and inert gas are activated by plasma to produce an activated etching gas. The plasma decomposes the etching gas into radical form (i.e., the activated etching gas). The plasma may be generated by applying RF or DC power. The plasma may be generated with a RF power ranging from about 25 W to about 10,000 W. The plasma may be generated or present within the reactor itself. The plasma may be generated in Dual CCP or ICP mode with RF applied at both electrodes. RF frequency of plasma may range from 200 KHz to 1 GHz. Different RF sources at different frequency can be coupled and applied at same electrode. Plasma RF pulsing may be further used to control molecule fragmentation and reaction at substrate. One of skill in the art will recognize methods and apparatus suitable for such plasma treatment.

Quadropole mass spectrometer (QMS), optical emission spectrometer, FTIR, or other radical/ion measurement tools may measure the activated etching gas to determine the types and numbers of species produced. If necessary, the flow rate of the etching gas and/or the inert gas may be adjusted to increase or decrease the number of radical species produced.

The disclosed etching gases may be mixed with other gases either prior to introduction into the plasma reaction chamber or inside the plasma reaction chamber. Preferably, the gases may be mixed prior to introduction to the chamber in order to provide a uniform concentration of the entering gas. In another alternative, the etching gas may be introduced into the chamber independently of the other gases such as when two or more of the gases react. In another alternative, the etching gas and the inert gas are the only two gases that are used during the etching process.

Exemplary other gases include, without limitation, oxidizers such as $O_2$, $O_3$, CO, $CO_2$, NO, $N_2O$, $NO_2$, and combinations thereof. The disclosed etching gases and the oxidizer may be mixed together prior to introduction into the plasma reaction chamber. Alternatively, the oxidizer may be introduced continuously into the chamber and the etching gas introduced into the chamber in pulses. The oxidizer may comprise between approximately 5% v/v to approximately 100% v/v of the mixture introduced into the chamber (with 100% v/v representing introduction of pure oxidizer for the continuous introduction alternative).

Other exemplary gases with which the etching gas may be mixed include additional etching gases, such as $cC_4F_8$, $C_4F_6$, $CF_4$, $CHF_3$, $CFH_3$, $CH_2F_2$, COS, $CS_2$, $CF_3I$, $C_2F_3I$, $C_2F_5I$, and $SO_2$. The vapor of the etching gas and the additional gas may be mixed prior to introduction to the plasma reaction chamber. The additional etching gas may comprise between approximately 1% v/v to approximately 99.9% v/v of the mixture introduced into the chamber.

The Si-containing layers and the activated etching gas react to form volatile by-products that are removed from the plasma reaction chamber. The amorphous carbon mask, antireflective coating, and photoresist layer are less reactive with the activated etching gas.

The temperature and the pressure within the plasma reaction chamber are held at conditions suitable for the silicon-containing layer to react with the activated etching gas. For instance, the pressure in the chamber may be held between approximately 0.1 mTorr and approximately 1000 Torr, preferably between approximately 1 mTorr and approximately 10 Torr, more preferably between approximately 10 mTorr and approximately 1 Torr, and more preferably between approximately 10 mTorr and approximately 100 mTorr, as required by the etching parameters. Likewise, the substrate temperature in the chamber may range between about approximately −196° C. to approximately 500° C., preferably between −120° C. to approximately 300° C., and more preferably between −10° C. to approximately 40° C. Chamber wall temperatures may range from approximately −196° C. to approximately 300° C. depending on the process requirements.

The reactions between the Si-containing layer and the activated etching gas results in anisotropic removal of the Si-containing layers from the substrate. Atoms of nitrogen, oxygen, and/or carbon may also be present in the Si-containing layer. The removal is due to a physical sputtering of Si-containing layer from plasma ions (accelerated by the plasma) and/or by chemical reaction of plasma species to convert Si to volatile species, such as $SiF_x$, wherein x ranges from 1-4.

The activated etching gas preferably exhibits high selectivity toward the mask and etches through the alternating layers of SiO and SiN resulting in a vertical etch profile with no bowing, which is important for 3D NAND applications. For other applications, such as DRAM and 2D NAND, for example, the plasma activated etching gas may selectively etch SiO from SiN. The plasma activated etching gas preferably selectively etches SiO and/or SiN from mask layers, such as amorphous carbon, photoresist, polysilicon, or silicon carbide; or from metal contact layers, such as Cu; or from channel regions consisting of SiGe or polysilicon regions.

The disclosed etch processes using the disclosed etching gases produce channel holes, gate trenches, staircase contacts, capacitor holes, contact holes, etc., in the Si-containing layers. The resulting aperture may have an aspect ratio ranging from approximately 10:1 to approximately 100:1 and a diameter ranging from approximately 40 nm to approximately 50 nm. For example, one of ordinary skill in the art will recognize that a channel hole etch produces apertures in the Si-containing layers having an aspect ratio greater than 60:1.

In one non-limiting exemplary plasma etch process, trans-1,1,1,4,4,4-hexafluoro-2-butene is introduced into a 200 mm Dual CCP plasma etch tool using a controlled gas flow device. The controlled gas flow device may be a mass flow controller. In case of high boiling point molecules, a special low pressure drop mass flow controller from Brooks Automation (No. GF120XSD), MKS Instruments, etc., may be used. The pressure of the plasma reaction chamber is set at approximately 30 mTorr. No gas source heating is necessary, as the vapor pressure of this compound is approximately 1340 torr at 25° C. The distance between the two CCP electrodes is kept at 1.35 cm and the top electrode RF power is fixed at 750 W. The bottom electrode RF power is varied to analyze the performance of the molecule. The plasma reaction chamber contains a substrate having 24 pairs of SiO and SiN layers thereon, similar to those shown in FIG. 1. Prior to this process, the ARC layer is removed by a fluorocarbon and oxygen-containing gas and the APF layer is removed by an oxygen-containing gas. Argon is independently introduced into the chamber at a 250 sccm flow rate. Trans-1,1,1,4,4,4-hexafluoro-2-butene is independently introduced into the chamber at 15 sccm. $O_2$ is independently introduced into the chamber at 0-20 sccm to determine optimum etching conditions. An aperture having an aspect ratio equal to or greater than 30:1 is produced, which may be used as a channel hole in vertical NAND.

In another non-limiting exemplary plasma etch process, hexafluoroisobutene is introduced into a 200 mm Dual CCP plasma etch tool using a controlled gas flow device. The controlled gas flow device may be a mass flow controller. In case of high boiling point molecules, a special low pressure drop mass flow controller from Brooks Automation (No. GF120XSD), MKS Instruments, etc., may be used. The pressure of the plasma reaction chamber is set at approximately 30 mTorr. No gas source heating is necessary, as the vapor pressure of this compound is approximately 900 Torr at 20° C. The distance between the two CCP electrodes is kept at 1.35 cm and the top electrode RF power is fixed at 750 W. The bottom electrode RF power is varied to analyze the performance of the molecule. The plasma reaction chamber contains a substrate having a thick SiO layer thereon, similar to the layer shown in FIG. 2. Prior to this process, the ARC layer is removed by a fluorocarbon and oxygen-containing gas and the APF layer is removed by an oxygen-containing gas. Argon is independently introduced into the chamber at a 250 sccm flow rate. Hexafluoroisobutene is independently introduced into the chamber at 15 sccm. $O_2$ is independently introduced into the chamber at 0-20 sccm to determine optimum etching conditions. An aperture having an aspect ratio equal to or greater than 10:1 is produced, which may be used as a contact hole in DRAM.

EXAMPLES

The following non-limiting examples are provided to further illustrate embodiments of the invention. However, the examples are not intended to be all inclusive and are not intended to limit the scope of the inventions described herein.

The following testing was performed using the SAMCO10-NR reactive ion etcher (RIE) or the Lam 4520XLE™ advanced dielectric etch system (200 mm dual frequency capacitively coupled plasma (CCP) ion etch).

Example 1

Figure 3:
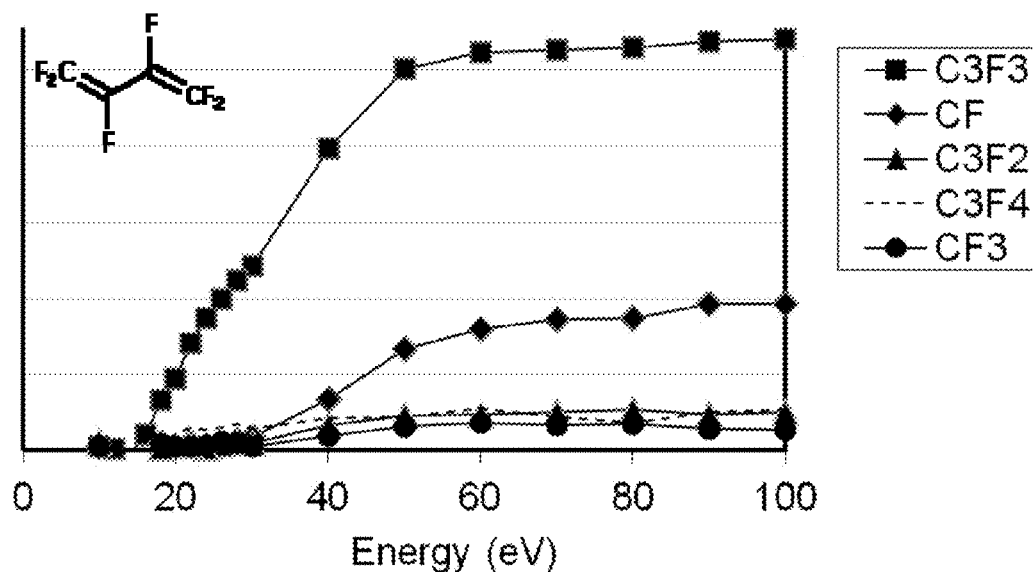
FIG. 3 is a mass spectrometry (MS) graph plotting the volume of species fractions produced by $C_4F_6H_2$ versus energy (in eV)
Figure 4:
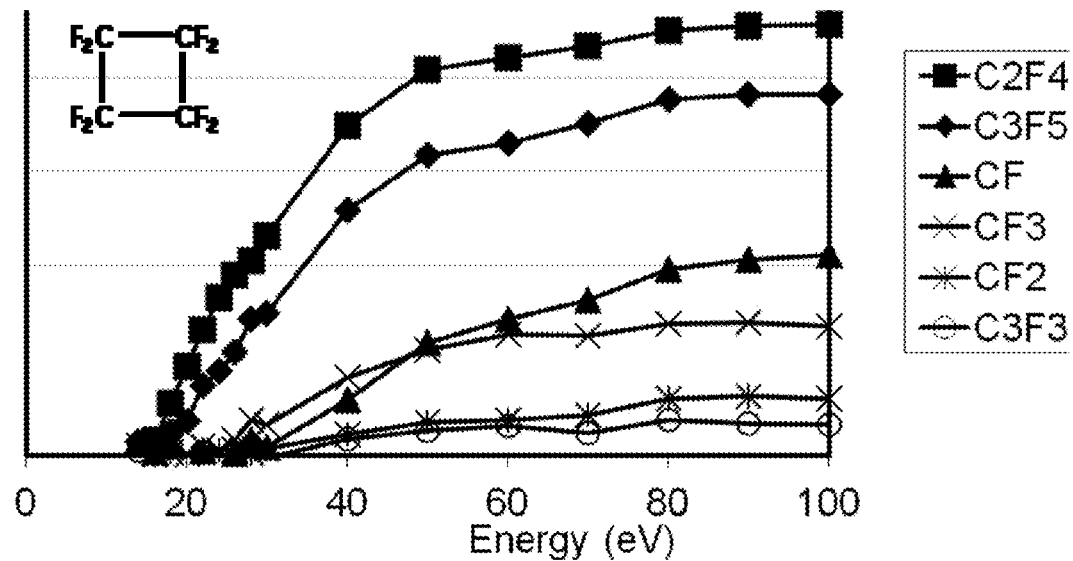
FIG. 4 is a MS graph plotting the volume of species fractions produced by $C_4F_8$ versus energy.

$C_4F_6$ and cyclic $C_4F_8$ were directly injected into a quadruple mass spectrometer (QMS) and data collected from 10-100 eV. The results are shown in FIGS. 3 and 4. Fragments from $C_4F_6$ have lower F:C ratio than the fragments from $C_4F_8$, which lead to higher polymer deposition rate and may improve selectivity.

Polymers were deposited by introduction into RIE plasma reaction chamber at 30 sccm with 1 sccm of Argon. The pressure in the chamber was set at 5 Pa. The plasma was set at 300 W. Polymers were deposited from $cC_4F_8$ at 100 nm/min and exhibited a 0.90 F:C ratio. Polymers were deposited from $C_4F_6$ at 280 nm/min and exhibited a 0.76 F:C ratio. $C_4F_6$ exhibited a much higher depositions rate and the resulting film showed a lower F:C ratio in the polymer, which may indicate increased cross-linking.

Example 2

Polymers were deposited from cyclic $C_4F_6H_2$ and cyclic $C_4F_5H_3$ under the same conditions as in Example 1 (i.e., 30 sccm etching gas, 1 sccm Ar, 5 Pa and 300 W). cyclic $C_4F_6H_2$ and cyclic $C_4F_5H_3$ are similar to cyclic $C_4F_8$, but have replaced 2 or 3 F atoms with H. Polymers were deposited from cyclic $C_4F_6H_2$ at 150 nm/min and exhibited a 0.59 F:C ratio. Polymers were deposited from cyclic $C_4F_5H_3$ at 200 nm/min and exhibited a 0.50 F:C ratio. Increasing the hydrogen content on the cyclic butane molecule resulted in increased polymer deposition rates and a decreased F:C ratio in the resulting polymer.

Example 3

Figure 5:
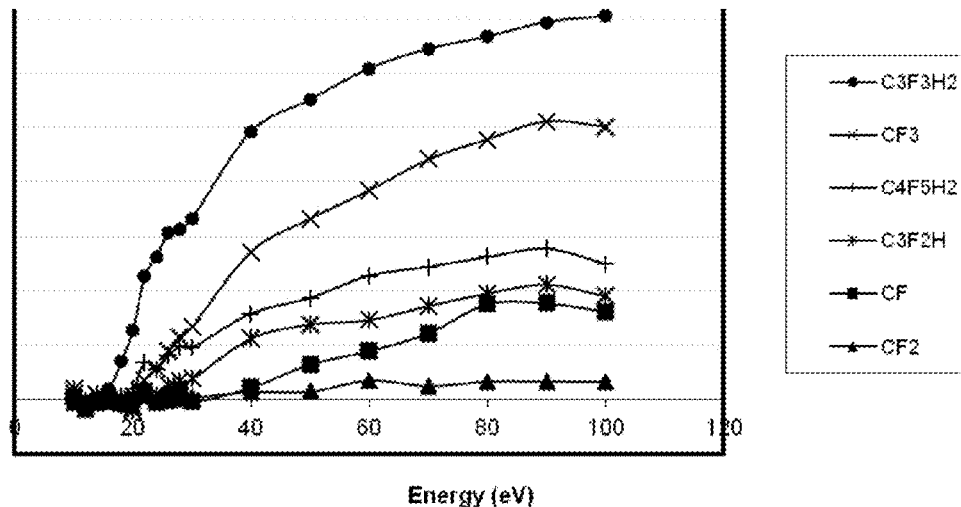
FIG. 5 is a MS graph plotting the volume of species fractions produced by trans-1,1,1,4,4,4-hexafluoro-2-butene versus energy.
Figure 6:
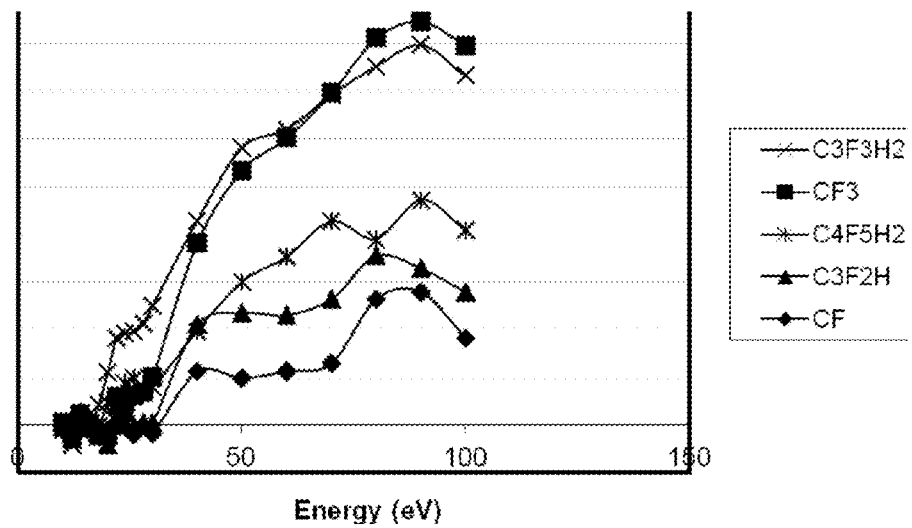
FIG. 6 is a MS graph plotting the volume of species fractions produced by hexafluoroisobutene versus energy.

Two molecules having the same stoichiometry (i.e., $C_4F_6H_2$) were directly injected into a quadruple mass spectrometer (QMS) and data collected from 10-100 eV. The results for trans-1,1,1,4,4,4-hexafluoro-2-butene (CAS No 66711-86-2) are shown in FIG. 5. The results for hexafluoroisobutene (CAS No 382-10-5) are shown in FIG. 6. At higher energies, more $CF_3$ fragments and less $C_3F_3H_2$ fragments were produced from hexafluoroisobutene than from trans-1,1,1,4,4,4-hexafluoro-2-butene. Fragments from $C_4F_6$ have lower F:C ratio than the fragments for $C_4F_8$, which lead to higher polymer deposition rate and may improve selectivity.

Polymers were deposited from both $C_4F_6H_2$ compounds under the same conditions as in Example 1 (i.e., 30 sccm etching gas, 1 sccm Ar, 5 Pa and 300 W). Polymers were deposited from trans-1,1,1,4,4,4-hexafluoro-2-butene at 250 nm/min and exhibited a 0.53 F:C ratio. Polymers were deposited from cyclic hexafluoroisobutene at 220 nm/min and exhibited a 0.53 F:C ratio.

Example 4

The following table summarizes test results for multiple etching gases:

TABLE 1

| Molecule[1] | H | C=C | 1st fragment at 100 ev | 2nd fragment at 100 ev | Polymer Dep Rate[2] | F:C Polymer |
|---|---|---|---|---|---|---|
| $cC_4F_8$ | No | No | $C_2F_4$ | $C_3F_5$ | 100 | 0.90 |
| $C_4F_6$ | No | Yes | $C_3F_3$ | CF | 280 | 0.76 |
| 66711-86-2 | Yes | Yes | $C_3H_2F_3$ | $CF_3$ | 250 | 0.53 |
| 382-10-5 | Yes | Yes | $CF_3$ | $C_3H_2F_3$ | 220 | 0.53 |
| $C_4F_8$ | No | Yes | $C_3F_5$ | $CF_3$ | 100 | 1.00 |
| 22819-47-2 | Yes | No | $C_2HF_3$ | $C_3H_2F_3$ | 150 | 0.59 |
| 23102-94-4 | Yes | No | $C_2HF_3$ | $C_3H_2F_3$ | 120 | 0.58 |
| 2253-02-3 | Yes | No | $C_3F_3$ | CF | 200 | 0.50 |

[1]$cC_4F_8$ = octafluorocyclobutane; $C_4F_6$ = hexafluorobutadiene, $C_4F_8$ = octafluoro-2-butene
[2]30 sccm etching gas, 1 sccm Ar, 5 Pa and 300 W Based on these results, the lowest polymer deposition rates showed the highest F:C ratio in the resulting polymer ($cC_4F_8$ and $C_4F_8$). The large difference in polymer deposition rates (in nm/min) between the four molecules having double bonds (i.e., rows 2-5) illustrates that inclusion of double bonds does not exclusively control polymerization. Instead, the deposition rate more closely followed fragmentation. In other words, molecules producing fragments having higher F:C ratios had reduced polymer deposition rates.

Example 5

Figure 7:
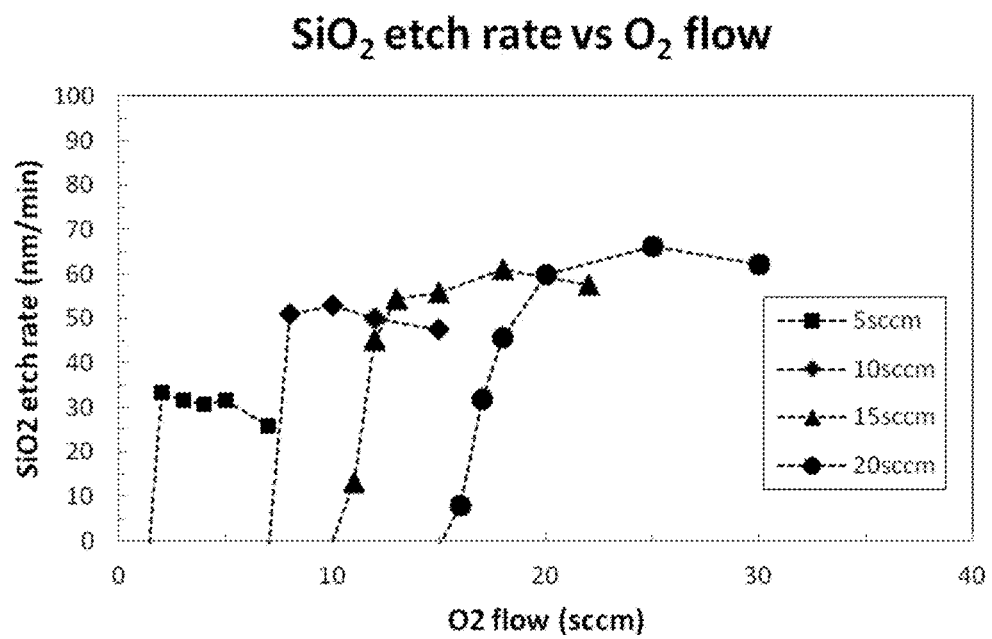
FIG. 7 is a graph of the $SiO_2$ etch rate versus oxygen flow (in sccm) for trans-1,1,2,2,3,4-hexafluorocyclobutane.
Figure 8:
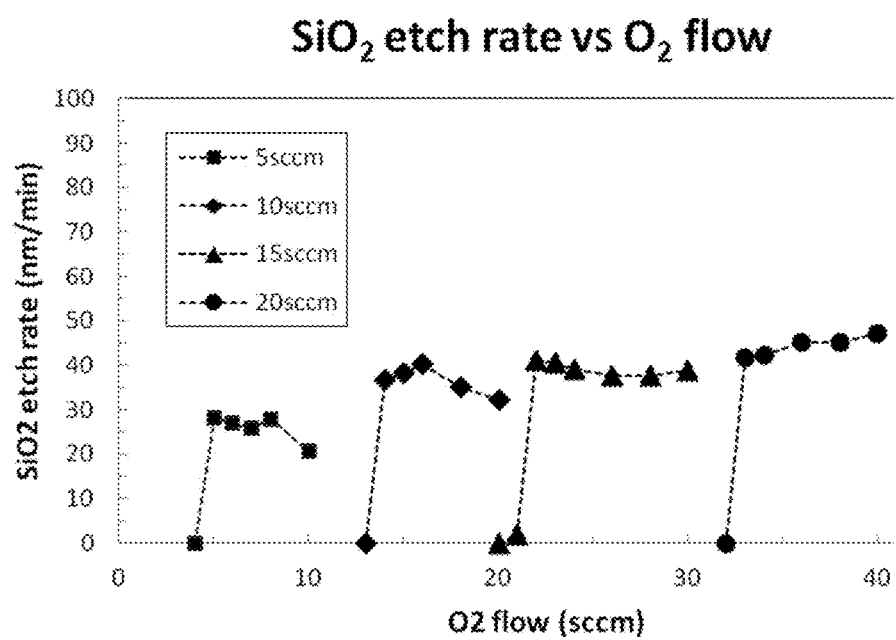
FIG. 8 is a graph of the $SiO_2$ etch rate versus oxygen flow for $cC_4F_5H_3$.

The effect of increasing H on $SiO_2$ etch rate was analyzed. A graph of the $SiO_2$ etch rate versus oxygen flow (in sccm) for trans-1,1,2,2,3,4-hexafluorocyclobutane is shown in FIG. 7. A graph of the $SiO_2$ etch rate versus oxygen flow for $cC_4F_5H_3$ is shown in FIG. 8. Replacing one F with H resulted in higher oxygen flow rates and narrower process windows.

Figure 9:
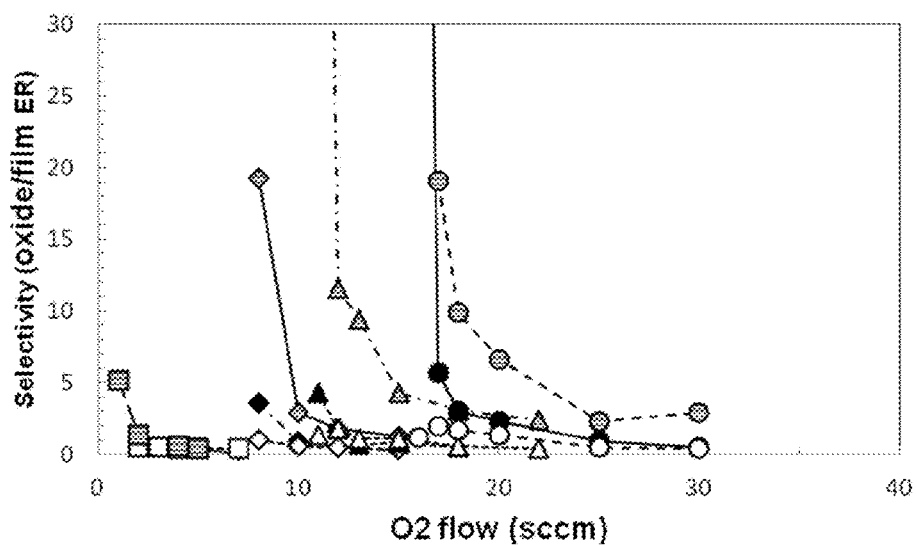
FIG. 9 is a graph of the selectivity versus oxygen flow for trans-1,1,2,2,3,4-hexafluorocyclobutane.
Figure 10:
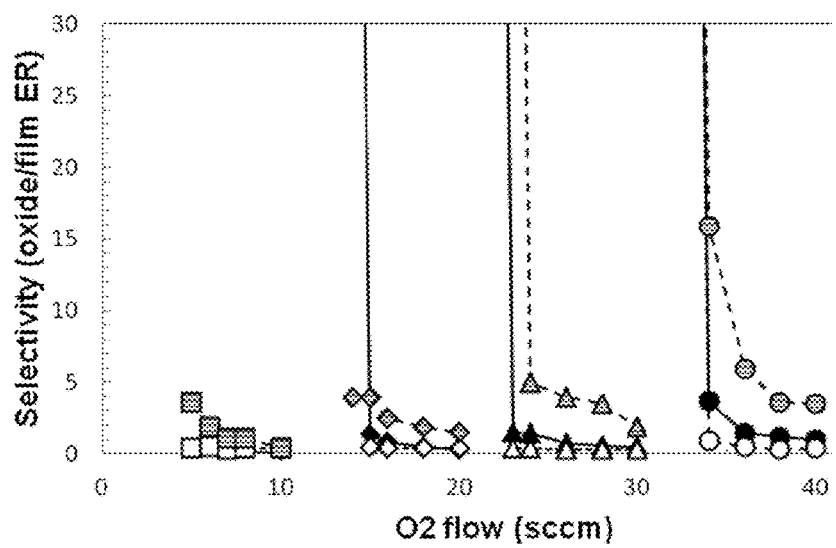
FIG. 10 is a graph of the selectivity versus oxygen flow for $cC_4F_5H_3$.

The effect of increasing H on oxide selectivity versus amorphous carbon (a-C), photoresist (PR), and nitride was also analyzed. A graph of the selectivity versus oxygen flow for trans-1,1,2,2,3,4-hexafluorocyclobutane is provide in FIG. 9. A graph of the selectivity versus oxygen flow for $cC_4F_5H_3$ is shown in FIG. 10. The molecule flow rates in FIGS. 9 and 10 are the same as those in FIGS. 7 and 8 (i.e., the square data on the left is from 5 sccm etch gas flow rate, the diamond data second from left is 10 sccm, the triangle data second from right is 15 sccm, and the circle data right is 20 sccm). In FIGS. 9 and 10, the solid symbols represent the silicon oxide/photoresist selectivity, the hollow symbols represent the silicon oxide/silicon nitride selectivity, and the shaded symbols represent the silicon oxide/amorphous carbon selectivity.

Example 6

The following table summarizes test results for multiple etching gases:

TABLE 2

| Molecule[3] | H | C=C | PR | a-C | N | $O_2$/gas ratio |
|---|---|---|---|---|---|---|
| $cC_4F_8$ | No | No | 3.0 | 5.0 | 3.2 | 0 |
| $C_4F_6$ | No | Yes | 1.1 | 4.3 | 2.3 | 1.5 |
| 66711-86-2 | Yes | Yes | 2.2 | 9.9 | 1.5 | 1.5 |
| 382-10-5 | Yes | Yes | 1.0 | 2.7 | 0.6 | 1.7 |
| $C_4F_8$ | No | Yes | 2.8 | 6.9 | 5.1 | 0.2 |
| 22819-47-2 | Yes | No | 5.6 | Inf | 2.2 | 1.4 |
| 23102-94-4 | Yes | No | 4.3 | 11.6 | 1.7 | 0.8 |
| 2253-02-3 | Yes | No | Inf | Inf | Inf | 1.5 |

[3]$cC_4F_8$ = octafluorocyclobutane; $C_4F_6$ = hexafluorobutadiene, $C_4F_8$ = octafluoro-2-butene The molecules were compared under similar $SiO_2$ etch rate conditions (ER 40-50 nm/min). The etching gas and oxygen flow rates were selected for best selectivity within the etch rate range. Other plasma conditions were fixed (i.e., Ar=150 sccm, 300 W, 5 Pa). The PR, a-C and N columns show the selectivity between $SiO_2$ and photoresist (PR), amorphous carbon (a-C), and silicon nitride (N). Based on these results, and particularly the results for $cC_4F_8$, 23102-94-4 (trans-1,1,2,2,3,4-hexafluorocyclobutane), and 2253-02-3 (1,1,2,2,3-pentafluorocyclobutane), increasing H increased mask selectivity. Additionally, even though 66711-86-2 (trans-1,1,1,4,4,4-hexafluoro-2-butene) and 382-10-5 (hexafluoroisobutene) have the same stoichiometry (i.e., $C_4F_6H_2$), the different structures resulted in significantly different results.

Example 7

Figure 11:
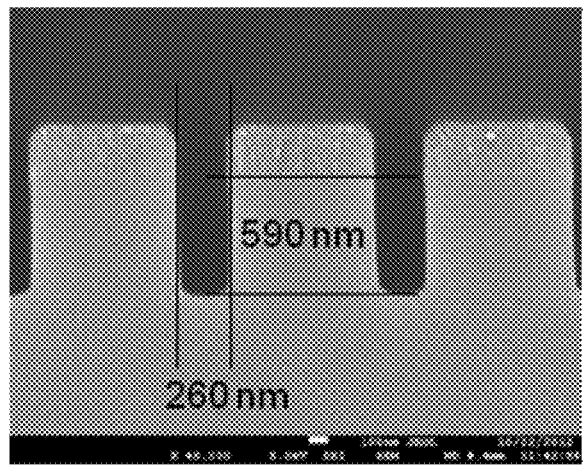
FIG. 11 is a scanning electron micrograph (SEM) of the results of a 10 minute etch using 15 sccm of $cC_4F_8$ and no oxygen.
Figure 12:
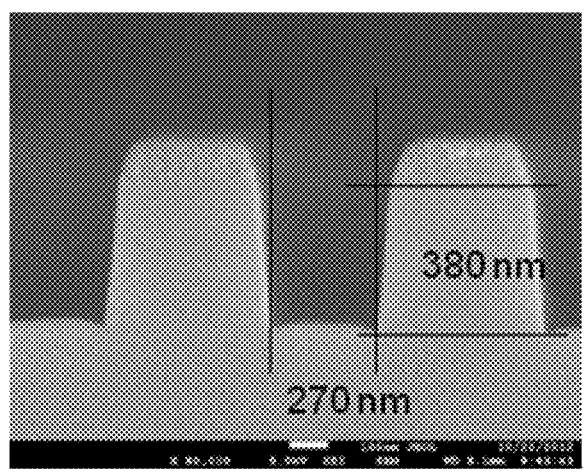
FIG. 12 is a SEM of the results of a 10 minute etch using 15 sccm of $cC_4F_6H_2$ and 12 sccm oxygen.
Figure 13:
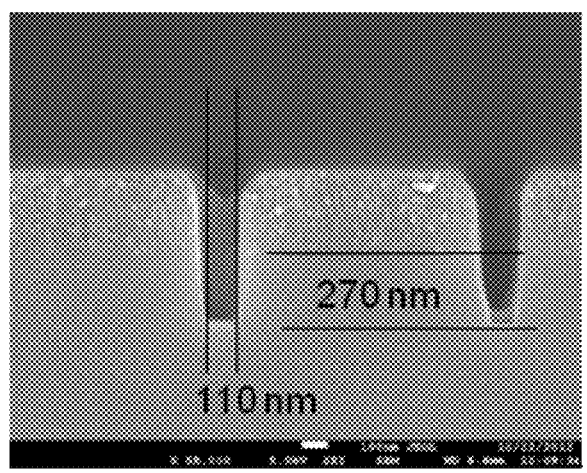
FIG. 13 is a SEM of the results of a 10 minute etch using 15 sccm of $cC_4F_5H_3$ and 22 sccm oxygen.

The effect of increased H content when etching a portion of a DRAM pattern stack was analyzed. The portion of the DRAM patterned stack consisted of P6100 patterns (2.9 kÅ) on an antireflective coating layer (ARC29a—0.8 kÅ), on a silicon oxynitride layer (1.0 kÅ), on an amorphous carbon layer (3.5 kÅ), on a 4 micron $SiO_2$ substrate (Silox). Argon was introduced at 150 sccm. The chamber was maintained at 5 Pa. The SAMCO RIE was set at 300 W. A scanning electron micrograph of the results of a 10 minute etch using 15 sccm of $cC_4F_8$ and no oxygen is provided in FIG. 11. A scanning electron micrograph of the results of a 10 minute etch using 15 sccm of $cC_4F_6H_2$ and 12 sccm oxygen is provided in FIG. 12. A scanning electron micrograph of the results of a 10 minute etch using 15 sccm of $cC_4F_5H_3$ and 22 sccm oxygen is provided in FIG. 13. As seen in the figures, increasing H promotes a tapered profile and results in a loss of etch rate (590 nm 380 nm→270 nm). Increased H content maintained a narrow trench. The 110 nm trench in FIG. 13 was present before the etch, whereas the trench was increased to 270 nm by $cC_4F_6H_2$ and 260 nm by $cC_4F_8$.

Example 8

Figure 14:
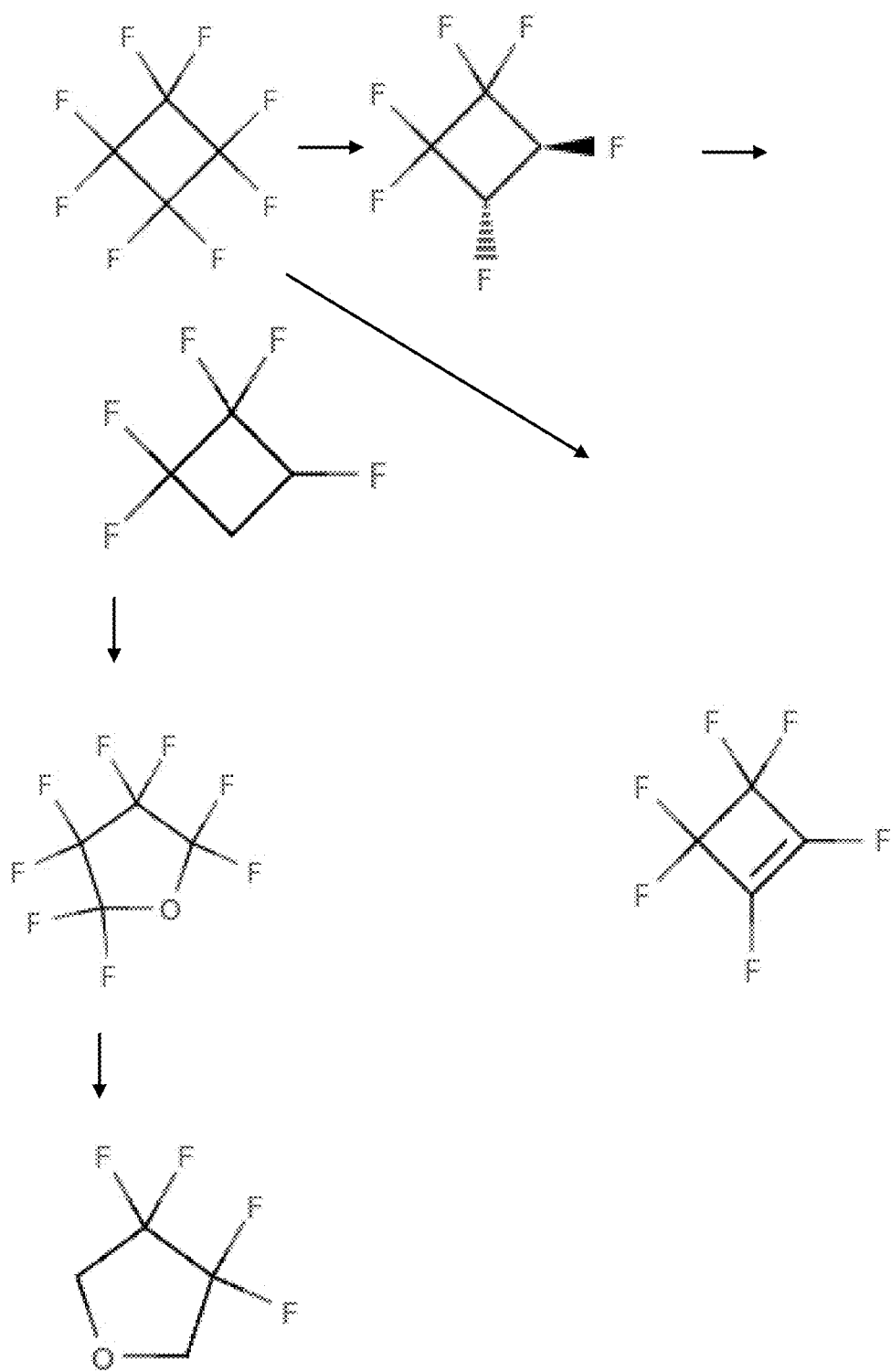
FIG. 14 is a flow chart showing the effect of H substitution, double bonds, and addition of 0 to a $C_4F_8$ molecule.

FIG. 14 is a flow chart showing the effect of H substitution, double bonds, and addition of O to a $C_4F_8$ molecule. $C_4F_8$ is shown in the top left corner of FIG. 14. An increased selectivity between SiO and mask and increased polymer deposition rate is seen when replacing 2 or 3 F atoms with hydrogen atoms (moving left to right along the top row). However, the increased H molecules also require an increase in $O_2$ dilution. An increased polymer deposition rate but similar selectivity and $O_2$ dilution requirements are seen when two F atoms are replaced by a double bond (i.e., changing the molecule from saturated to unsaturated)(moving from the middle of the first row to the right side of the second row). Addition of oxygen results in poor selectivity and no polymer deposition (moving down the column on the left side of the page). An increased selectivity and polymer deposition rate is seen, but in a narrow process window, when fluorine atoms are replaced by hydrogen atoms on the oxygen-containing molecule (bottom left side of page).

Example 9

The deposition and etch rates for cyclic $C_4F_8$ (octafluorocyclobutane), $C_4F_6$ (hexafluoro-1,3-butadiene), and linear $C_4F_6H_2$ (CAS 66711-86-2) were measured.

The source or RF power of the Lam etch system was set at 750 W and the bias power was set at 1500 W. The pressure was set at 30 mTorr. The distance between the plates was set at 1.35 cm. Oxygen was introduced at a flow rate of 15 sccm. Argon was introduced at a flow rate of 250 sccm. Each etch gas was introduced at 15 sccm. The results are shown in the following table:

TABLE 3

| Molecule[4] | SiO2 Etch Rate | Selectivity a-C | Selectivity SiN | Polymer Dep Rate |
|---|---|---|---|---|
| $cC_4F_8$ | 440 | 4 | 2 | 56 |
| $C_4F_6$ | 501 | 8 | — | 467 |
| 66711-86-2 | 390 | 12 | 2 | 250 |

[4]$cC_4F_8$ = octafluorocyclobutane; $C_4F_6$ = hexafluorobutadiene 66711-86-2 (trans-1,1,1,4,4,4-hexafluoro-2-butene) has better selectivity between silicon oxide and amorphous carbon than the conventional $cC_4F_8$, with a similar silicon oxide etch rate. 66711-86-2 also has a higher deposition rate than $cC_4F_8$.

Example 10

The etch rate of $SiO_2$, SiN, p-Si (polysilicon), and a-C (amorphous carbon) using 1,1,1,2,4,4,4-heptafluoro-2-butene was measured.

The source or RF power of the Lam etch system was set at 750 W and the bias power was set at 1500 W. The pressure was set at 30 mTorr. The distance between the plates was set at 1.35 cm. Oxygen was introduced at a flow rate of 15 sccm. Argon was introduced at a flow rate of 250 sccm. 1,1,1,2,4,4,4-heptafluoro-2-butene was introduced at a flow rate of 15 sccm. 1,1,1,2,4,4,4-heptafluoro-2-butene etched the $SiO_2$ layer at the rate of 550 nm/min. 1,1,1,2,4,4,4-heptafluoro-2-butene etched the SiN layer at the rate of 150 nm/min. 1,1,1,2,4,4,4-heptafluoro-2-butene etched the p-Si layer at the rate of 50 nm/min. 1,1,1,2,4,4,4-heptafluoro-2-butene etched the a-c layer at the rate of 75 nm/min. 1,1,1,2,4,4,4-heptafluoro-2-butene shows good selectivity between $SiO_2$ and p-Si and a-c.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

What is claimed is:

1. A method for etching silicon-containing films, the method comprising,
   introducing an etching gas into a plasma reaction chamber containing a silicon-containing film on a substrate, wherein the etching gas is selected from the group consisting of trans-1,1,1,4,4,4-hexafluoro-2-butene; cis-1,1,1,4,4,4-hexafluoro-2-butene; hexafluoroisobutene (CAS No. 382-10-5); pentafluorocyclobutane (1,1,2,2,3-); and tetrafluorocyclobutane (1,1,2,2-);
   introducing an inert gas into the plasma reaction chamber; and
   activating a plasma to produce an activated etching gas capable of selectively etching the silicon-containing film from the substrate.

2. The method of claim 1, further comprising removing volatile by-products from the chamber, wherein the activated etching gas selectively reacts with the silicon-containing film to form volatile by-products.

3. The method of claim 1, wherein the inert gas is selected from the group consisting of He, Ar, Xe, Kr, and Ne.

4. The method of claim 1, wherein the inert gas comprises approximately 50% v/v to approximately 95% v/v of a total volume of etching gas and inert gas introduced into the plasma reaction chamber.

5. The method of claim 1, further comprising introducing an oxidizer into the plasma reaction chamber.

6. The method of claim 5, wherein the oxidizer is selected from the group consisting of $O_2$, CO, $CO_2$, NO, $N_2O$, and $NO_2$.

7. The method of claim 5, wherein the oxidizer comprises approximately 5% v/v to approximately 100% v/v of a total volume of etching gas and oxidizer introduced into the plasma reaction chamber.

8. The method of claim 5, wherein the etching gas is trans-1,1,1,4,4,4-hexafluoro-2-butene.

9. The method of claim 5, wherein the etching gas is hexafluoroisobutene.

10. The method of claim 1, wherein the silicon-containing film comprises a layer of silicon oxide, silicon nitride, polysilicon, or combinations thereof.

11. The method of claim 10, wherein the silicon-containing film is selectively etched from an amorphous carbon layer.

12. The method of claim 10, wherein the silicon-containing film is selectively etched from a photoresist layer.

13. The method of claim 10, wherein the silicon-containing film is selectively etched from a polysilicon layer.

14. The method of claim 10, wherein the silicon-containing film is selectively etched from a metal contact layer.

15. The method of claim 1, wherein the method produces an aperture in the silicon-containing film having an aspect ratio between approximately 10:1 and approximately 100:1.

16. The method of claim 1, further comprising improving selectivity by introducing a second gas into the plasma reaction chamber, wherein the second gas is selected from the group consisting of $cC_4F_8$, $C_4F_6$, $CF_4$, $CHF_3$, $CFH_3$, $CH_2F_2$, COS, $CS_2$, $CF_3I$, $C_2F_3I$, $C_2F_5I$, and $SO_2$.

17. The method of claim 1, wherein the etching gas is trans-1,1,1,4,4,4-hexafluoro-2-butene.

18. The method of claim 1, wherein the etching gas is hexafluoroisobutene.

19. A method for etching a silicon oxide film from an amorphous carbon substrate, the method comprising, introducing a trans-1,1,1,4,4,4-hexafluoro-2-butene etch gas into a plasma reaction chamber containing the silicon oxide film on the amorphous carbon substrate;

introducing an inert gas into the plasma reaction chamber; and etching the silicon oxide film from the amorphous carbon substrate by activating a plasma.

20. A method for etching silicon oxide and silicon nitride films from a substrate, the method comprising, introducing a hexafluoroisobutene etch gas into a plasma reaction chamber containing the silicon oxide and silicon nitride films on the substrate;

introducing an inert gas into the plasma reaction chamber; and etching the silicon oxide and silicon nitride films from the substrate by activating a plasma.

* * * * *